(12) United States Patent
Roston et al.

(10) Patent No.: US 7,582,788 B2
(45) Date of Patent: Sep. 1, 2009

(54) PROCESS FOR PREPARATION OF ALKOXYSILANES

(75) Inventors: William A. Roston, Southfield, MA (US); Robert D. Cody, Stratford, CT (US); Matthew Daniel Bowman, Vernon, CT (US)

(73) Assignee: Roston Family LLC, Southfield, MA (US)

( * ) Notice: Subject to any disclaimer, the term of this patent is extended or adjusted under 35 U.S.C. 154(b) by 0 days.

(21) Appl. No.: 11/973,239

(22) Filed: Oct. 5, 2007

(65) Prior Publication Data

US 2008/0132721 A1     Jun. 5, 2008

Related U.S. Application Data

(60) Provisional application No. 60/872,383, filed on Dec. 1, 2006.

(51) Int. Cl.
    *C07F 7/04* (2006.01)
(52) U.S. Cl. ........................ 556/415; 556/470
(58) Field of Classification Search ................ 556/415, 556/470
    See application file for complete search history.

(56) References Cited

U.S. PATENT DOCUMENTS

| | | | |
|---|---|---|---|
| 3,071,700 A | 1/1963 | Smith | 387/88.5 |
| 3,775,077 A | 11/1973 | Niscastro, Jr. et al. | 65/18 |
| 3,775,457 A | 11/1973 | Muraoka et al. | 260/448.8 |
| 4,727,173 A | 2/1988 | Mendicino | 556/470 |
| 4,762,938 A | 8/1988 | Frölen | 556/470 |
| 5,103,034 A | 4/1992 | Cho et al. | 556/470 |
| 5,527,937 A | 6/1996 | Standke et al. | 556/470 |
| 5,728,858 A | 3/1998 | Lewis et al. | 556/470 |
| 5,783,720 A | 7/1998 | Mendicino et al. | 556/470 |
| 6,242,628 B1 | 6/2001 | Kropfgans et al. | 556/471 |
| 6,380,414 B2 | 4/2002 | Brand | 556/470 |
| 6,410,771 B1 | 6/2002 | Brand | 556/470 |
| 6,580,000 B1 | 6/2003 | Anderson et al. | 556/470 |
| 6,680,399 B2 | 1/2004 | Anderson et al. | 556/470 |

FOREIGN PATENT DOCUMENTS

| | | |
|---|---|---|
| CN | 1810811 | 8/2006 |
| EP | 0517398 A | 5/1992 |
| JP | 55-2641 | 1/1980 |
| JP | 55-28928 | 2/1980 |
| JP | 55-28929 | 2/1980 |
| JP | 55-76891 | 6/1980 |
| JP | 57-108094 | 7/1982 |
| JP | 62-96433 | 5/1987 |
| JP | 101168084 A | 11/1989 |
| RU | 2157375 | * 10/2000 |
| RU | 2196142 | * 1/2003 |

OTHER PUBLICATIONS

Peng et al., Effect of microwave pretreatment on synthesis of trimethoxysilane, Jingxi Huagong (2004), 21(3), 213-215.*
Majetich et al., The Use of Microwave Heating to Promote Organic Reactions, Journal of Microwave Power and Electromagnetic Energy, 30, 1, 1995, 27-45.*
Gedye et al., The Rapid Synthesis of Organic Compounds in Microwave Ovens II, Can. J. Chem., 66, 1988, 17-26.*
Whittaker et al., The Application of Microwave Heating To Chemical Syntheaes, Journal of Microwave Power and Electromagnetic Energy, 29, 4, 1994, 195-219.*
International Search Report for corresponding International Patent Application No. PCT/US07/21465 dated Aug. 18, 2008.

* cited by examiner

*Primary Examiner*—Sikarl A. Witherspoon
*Assistant Examiner*—Chukwuma O Nwaonicha
(74) *Attorney, Agent, or Firm*—Ohlandt, Greeley, Ruggiero & Perle, L.L.P.

(57) ABSTRACT

Alkoxysilanes are prepared by a process which uses microwave or RF energy. Thus, silicon metal and a copper catalyst are exposed to microwave radiation in the presence of an appropriate hydroxy compound, such as, an alcohol, and a catalyst, to yield the corresponding trialkoxysilane. The desired alkoxysilanes are prepared with high selectivity and at lower temperatures and shorter times than traditional approaches allow.

30 Claims, No Drawings

PROCESS FOR PREPARATION OF ALKOXYSILANES

CROSS-REFERENCE TO RELATED APPLICATION

This application is related to, and claims priority in, U.S. Provisional Patent Application No. 60/872,383, filed on Dec. 1, 2006, the disclosure of which is incorporated in its entirety by reference herein.

BACKGROUND OF THE INVENTION

1. Field of the Invention

The present invention generally relates to a process for the preparation of alkoxysilanes, most preferably trialkoxysilanes, utilizing microwave or RF energy. More particularly, the present invention relates to a process for the preparation of alkoxysilanes wherein silicon metal and a copper catalyst are exposed to microwave or RF radiation in the presence of an appropriate alcohol and a catalyst to yield the corresponding trialkoxysilane.

2. Description of the Prior Art

Alkoxysilanes, specifically trialkoxysilanes, and particularly trimethoxysilane and triethoxysilane are important items of commerce. The alkoxysilanes serve as raw materials in the production of coupling agents that are critical to many industrial segments including adhesive and sealants, coatings, plastics, fabrics, medical devices, cosmetics and others. Although there are many reports of methods to produce trialkoxysilanes none provide a simple and sustainable process.

Alkoxysilanes are well known in industry and are used in the preparation of organosilanes that are suitable for use in many applications including their use as coupling agents.

Traditional chemical approaches to alkoxysilanes include the hydrochlorination of silicon metal with subsequent hydrosilylation and esterification. The first step of this three step process requires a significant equipment investment due to the high temperatures required and corrosion which results.

A direct two step method was subsequently developed which involved the direct reaction of alcohols with silicone metal. This process was limited to methanol as alcohols of higher chain length proved to be unreactive or to have little reactivity towards silicon metal under the process conditions. The use of methanol, while useful in creating a trialkoxysilane which can be further reacted, is limited by the elimination of the toxic methanol as a byproduct upon cure or by reaction with moisture.

Improvements in the direct chemistry approach that allowed preparation with higher chain alcohols utilized a heat transfer agent, such as, a solvent, temperatures of 230° C. to 240° C., and very long reaction times. The catalyst choice is reported to be critical as the catalyst must have solubility in the solvent. Copper II salts of carboxylic acids were found to perform effectively. Both the direct process and the hydrochlorination process are reported to be used within the industry. Fluidized bed processes are also reported, however, they are reported to suffer from hot spots and a significant reduction in selectivity.

U.S. Pat. No. 3,071,700 describes a process for the production of alkoxysilanes where finely divided silicon is reacted in the liquid phase by contact with alcohols and phenols yielding a mono-, di-, tri- and tetramethoxysilanes.

The direct synthesis of trialkoxysilanes is disclosed in U.S. Pat. No. 3,775,077 by Rochow. The patent teaches the preparation of trialkoxysilanes by directly reacting a copper-silicon mass suspended in a silicone oil with an alcohol at 250° C.-300° C. The copper-silicon mass contains about 10 weight percent copper and is prepared by heating the copper-silicon mass in excess of 1000° C. The method results in low yields of the trialkoxysilane.

U.S. Pat. No. 3,775,457 teaches the use of polyaromatic hydrocarbon oils as solvents for the direct process using finely divided silicon with cuprous chloride as catalyst. Although the cuprous chloride results in a yield improvement versus the activated copper-silicon mass of U.S. Pat. No. 3,775,077 the use of cuprous chloride results in the need for expensive corrosion resistant materials of construction for the reactor and related equipment. Additionally, the use of cuprous chloride acts to catalyze the reaction of the trialkoxysilane to the tetraalkoxysilane which reduces the yield of the trialkoxysilane.

Additionally, when methanol is a reactant for producing trimethoxysilane, the use of cuprous chloride leads to formation of HCl which will react with some of the methanol to yield methyl chloride and water. This result leads to inefficiency with regard to the methanol usage. Water produced by the reaction can react with the trialkoxysilane and tetraalkoxysilane to produce soluble and gelled siloxanes thus further reducing the efficiency of the reaction. The presence of water can also adversely affect the silicon conversion. Other patents, for example the Japanese Kokai Tokkyo Koho 55-28928, 55-28929, 55-76891, 57-108094, and 62-96433 which disclose the use of cuprous or cupric chloride are subject to the same limitations.

U.S. Pat. No. 4,727,173 discloses the use of copper (II) hydroxide as catalyst which avoids the limitations associated with cuprous chloride and provides high selectivity to the trialkoxysilanes. The preferred solvents are diphenyl ether, polyaromatic hydrocarbons and alkylated benzenes such as dodecylbenzene. However, when copper (II) hydroxide is used in combination with alkylated benzenes, such as dodecylbenzene, the direct synthesis of trialkoxysilanes becomes unstable after about 25-35 weight percent of the silicon has been reacted. When methanol is the alcohol reactant at temperatures above 220° C., the trimethoxysilane content declines after approximately 90-95 weight percent to approximately 50-60 weight percent and recovers again to 80-95 weight percent after approximately 60 percent silicon conversion. Coupled with the loss of selectivity is the enhanced formation of methane, water and dimethyl ether. Methane and dimethyl ether formation represent inefficient use of the alcohol reagent. The problems associated with water generation are noted above.

Alcohol dehydration and dehydrogenation are troublesome with the use of ethanol and other higher homologs in the direct synthesis approach. At some temperatures (>250° C.) alkenes, and aldehydes are formed in significant amounts at the expense of the desired trialkoxysilane. The presence of these undesired products can also have a negative effect on the catalytic activity in terms of inhibition. At lower temperatures (<220° C.) the alcohol decomposition products are less prevalent but the direct synthesis is impractically slow. Japanese Kokai Tokkyo Koho 55-2641 discloses the use of cyclic ethers to improve reactivity and selectivity to triethoxysilane when the direct synthesis is conducted in dodecylbenzene at these low temperatures. Cyclic ethers such as dibenzo-18-crown-6 are quite expensive. Others such as 12-crown-4 are toxic.

A process for producing controlled selectivity mixtures of trialkoxysilane and tetraalkoxysilane is described in U.S. Pat. No. 4,762,939. The use of a mixed solvent system is useful in controlling the selectivity between the tri- and tetra-substituted products over a wide range. An inert solvent along with a solvent that promotes the reactivity of the trialkoxysilane with alcohol to produce the tetraalkoxysilane represent the preferred mixture. The teachings are especially designed to produce the tetraalkoxysilane.

U.S. Pat. No. 4,762,938 describes the preparation of alkoxysilanes by reacting halosilanes with monhydric alcohols and a trialkyl phosphite. In reactions using chlorosilanes, the hydrogen chloride that is formed during the esterification must be removed quickly from the reaction mixture in order to ensure complete reaction, to obtain a hydrogen chloride free product and to prevent undesirable side reactions. To achieve this it is often necessary to utilized complex and expensive manufacturing processes and plants and is difficult to achieve in an industrial scale. In addition the resulting product mixture contains the strong smelling trialkyl phosphite and the close boiling points between the phosphite and products may make purification difficult.

A process for producing trialkoxysilanes including an activation step wherein elemental silicon and copper catalysts are activated, a reaction step wherein an alcohol is reacted with the activated silicon/catalyst complex and a purification step wherein a halide is introduced into the reaction mixture is described in U.S. Pat. No. 4,931,578. This process results in a more stable product. Although high levels of silicon conversion and high selectivity are reported, the activation sequence and overall time make this process unattractive.

U.S. Pat. No. 5,103,034 discloses a process to make alkyldialkoxysilanes and trialkoxysilanes using silicon metal and either an alcohol, an acetal and/or an orthocarboxylic acid ester. Over all conversions of silicon and the selectivity to the trialkoxysilane are both very low.

U.S. Pat. No. 5,527,937 discloses a process for the Direct Synthesis of triethoxysilane wherein copper chloride is the catalyst and tri- or tetra-toluenes and/or their alkyl substituted derivatives are the solvents and dimethylsilicone is used as an antifoaming agent. The polyphenyl solvents are expensive heat transfer agents.

U.S. Pat. No. 5,728,858 teaches the use of a reducing agent to improve the activity of the silicon-copper catalyst. Improved yields of the trialkoxysilanes are cited with the use of the alkylated benzene and polyaromatic solvents. Activation of the silicon-copper catalyst can generate impurities that can adversely effect the reaction so efforts must be taken to remove them prior to the reaction. Reaction times are also very long making the process impractical from a commercial perspective.

The use of surface active additives in the direct synthesis of trialkoxysilanes is described in U.S. Pat. No. 5,783,720. The additives which are described as silicone antifoaming compounds and fluorosilicone polymers are stated to shorten the reaction induction time and time to steady state rates. Extreme care must be taken to ensure the products are not contaminated with the surface-active agents and that such surface-active agents do not induce any adverse pathways in the reaction. Contamination of the products can cause severe application performance problems.

U.S. Pat. No. 6,242,628 describes the preparation of alkoxysilanes by reaction of a chlorosilane and an alcohol. The process as described is cited as producing low acidic chloride containing products and involves addition of a metal alcoholate to the separated product to neutralize the acid component followed by reduced pressure distillation. If the neutralization is carried out at relatively high temperatures the neutralization process gives rise to secondary reactions which result in a reduction of product yield. The presence of the acid chloride in the reaction mixture requires the use of expensive corrosion resistant equipment.

U.S. Pat. No. 6,380,414 describes a process wherein trialkoxysilanes are prepared by the reaction of silicon metal and an alcohol in the presence of copper (II) oxide. The use of copper (II) oxide is described to produce an alkoxysilane in high conversion from the silicon and with high selectivity with regard to trialkoxysilane to tetraalkoxysilane. The process is limiting as the copper (II) oxide is required to be of a very narrow particle size distribution and is preferably generated from freshly precipitated copper (II) oxide. Additionally, the time to reach conversion is very long requiring 22 to 28 hours.

JP-A-101168084 relates to the preparation of trialkoxysilanes by reacting silicon metal and alcohol over a copper (II) oxide catalyst which has water content of <3000 ppm. The low water content of the catalyst may require a thermal pretreatment of the catalyst and hence an additional reaction step.

EP-A 0 517 398 discloses a process for preparing trialkoxysilanes by reacting silicon with a solution of hydrogen fluoride or a salt which can be hydrolyzed to form hydrogen fluoride in a liquid primary or secondary alcohol, with or without the addition of a copper catalyst. However, the use of hydrogen fluoride is problematic, since hydrogen fluoride is extremely toxic and can attack glass. Furthermore, the actual reaction has to be preceded by a pretreatment step in this process since $CuF_2$ itself is inactive as a catalyst.

The use of a copper salt as catalyst whose anion contains at least one non-hydrolyzable fluorine atom for preparing trialkoxysilanes is disclosed in U.S. Pat. No. 6,410,771.

The non-hydrolyzable fluorine containing catalyst can also be used with additional copper containing catalysts. Good conversion and selectivity are described, however, very long reaction times are required to complete the reaction.

U.S. Pat. No. 6,580,000 and U.S. Pat. No. 6,680,399 disclose the preparation of alkoxysilanes by reacting silicon metal with an alcohol in the presence of a cupric bis(diorganophosphate) catalyst. The reaction is carried out in a polymeric form of ethyl orthosilicate as solvent. The preferred catalyst is cupric bis(diethyl phosphate). The use of the cupric bis(diorganophosphate) while favoring the selectivity of the trialkoxysilane does not afford the selectivity associated with other catalysts. Additionally, the ethyl orthosilicate solvent contains 28% of one of the reaction products, tetraethoxysilane (TEOS). The presence of the product (TEOS) in the reaction mixture makes quantitative analysis difficult and shifts the equilibrium to the tetra substituted silicon. Very long reaction times are required to achieve the results disclosed.

Lipschutz, et al., in *Organic Letters,* 5(17), 3085-3088, describes the reduction of dialkyl ketones to trialkylsilyl ethers using copper hydride-ligand complex under classical synthetic conditions and with sodium tert-butoxide in the presence of microwave radiation. Microwave and RF irradiation can accelerate the rate of chemical reactions by way of localized superheating of the reaction mixture. In the presence of a metal catalyst this effect is further enhanced. In many cases, microwave and RF heating is more energy efficient than conventional heating methods. Silicon nitride and oxide films and nanowires have been prepared in a microwave plasma environment. Crystalline silicon nanoparticles have been produced by the microwave decomposition of silane. However, there are no reports of a process for preparation of alkoxysilanes which employs microwave or RF irradiation.

In view of the deficiencies of the known art, there remains a need for a simple direct synthesis process without the need for pre or post treatment, which can be completed in a reasonable period of time with high conversion and selectivity towards the trialkoxysilane. The use of controlled microwave or RF generator provides such a process directed to preparation of alkoxysilanes by applying microwave or RF irradiation to silicon and alcohol in the presence of a catalyst.

SUMMARY OF THE INVENTION

Accordingly, the present invention provides a process for preparation of an alkoxysilane represented by the formula:

$$H_nSi(OR)_{4-n}$$

wherein n is from 0 to about 2; and wherein each R is independently selected from a linear, branched or cyclic alkyl of 1-12 carbon atoms, aryl, and acyl, wherein at least one of the alkyl, aryl and acyl groups is optionally substituted by at least one alkyl, alkoxy, halo, cyano or aryl;

the process including the step of:

contacting elemental silicon and a hydroxy compound represented by the formula:

$$ROH$$

wherein R is selected from a linear, branched or cyclic alkyl of 1-12 carbon atoms, aryl, and acyl, wherein at least one of the alkyl, aryl and acyl groups is optionally substituted by at least one alkyl, alkoxy, halo, cyano or aryl;

wherein the contacting is carried out in the presence of a catalyst including at least one of copper, zinc, and nickel, and a non-ionizing radiation selected from microwave, radio frequency (RF), and a combination thereof, at a temperature, pressure, and length of time sufficient to form the alkoxysilane.

Such alkoxysilanes have not been previously prepared by the use of microwave and/or RF energy. The use of microwave and/or RF energy overcomes the problems associated with the prior art.

The use of microwave energy in the present invention yielded the desired alkoxysilane products with high conversion and high selectivity.

Further, because an effective conversion can be achieved at much lower temperatures and shorter times than previously known, the present process produces fewer and lower levels of undesirable by-products and offers significant economic advantages.

Still further, the present process affords a simple, clean, rapid, sustainable, low temperature, short induction time, short reaction time, high conversion, and highly selective route to alkoxysilanes.

DETAILED DESCRIPTION

The present invention provides a process to prepare trialkoxysilanes of the formula $HSi(OR)_3$ wherein R is an alkyl group containing at least 1 carbon atom. The production of the trialkoxysilane and tetraalkoxysilane is preferred with the production of the trialkoxysilane being particularly preferred.

The alkoxysilane is represented by the formula:

$$H_nSi(OR)_{4-n}$$

Preferably, n is from 0 to about 2, more preferably n is from about 1 to about 2, and most preferably, n is 0, 1 or 2.

Preferably, each R is independently selected from methyl, ethyl, propyl, and butyl.

Preferably, the hydroxy compound is selected from methanol, ethanol, and a mixture thereof. The hydroxy compound can be a mixture of at least two alcohols.

Preferably, the alkoxysilane is triethoxysilane or trimethoxysilane.

The process includes reacting an alcohol with a slurry of silicon metal and a copper catalyst with or without an inert solvent in the presence of a microwave field or RF field.

The process of the present invention produces preferably the trialkoxysilane in high selectivity with high silicon conversion in relatively short time cycles.

Activation of the silicon metal and catalyst are also not required. The process can be run as a batch, semi-continuous or continuous process.

Metallic silicon used as one of the reactants in the present invention is suitably one having a purity of 80% by weight or more. Metallic silicon having up to about 1% by weight of Al, Fe, Ca, Mg, Zn, Ti, Cr, Ni, Mn, Ba, Cu, Zr and other impurities can be used. The metallic silicon used in the invention is suitably granular. There is little limitation of the size of the metallic silicon particle. Particle size of the metallic silicon can range from 50 to 700 microns, with particle size of about 200 microns being preferred.

The alcohols used in the invention having one or more carbon atoms can be straight chain or branched chain, including, methanol, ethanol, n-propanol, isopropanol, n-butanol, sec-butanol, isobutanol, tert-butanol and the like. Among the alcohols methanol and ethanol are most preferred. The alcohols are preferably of a purity of 95% or more. The alcohols do not need to be anhydrous but should contain a low level of water preferably of about 500 ppm. Alcohols that are not anhydrous can be treated with a dehydrating agent to reduce the water content.

The feed rate of the alcohol to the reaction system can vary depending upon the reaction with the minimum feed rate being at least from 0.2 mL/min. The alcohol can be diluted with an inert solvent or can be accompanied by an inert gas feed.

The catalyst used in this invention is not particularly restricted and can be those conventionally used, such as copper catalysts, zinc catalysts, nickel catalysts and the like.

Preferably, the catalyst is selected from copper(0), copper (I) salts, copper(II) salts, copper (II) hydroxide, zinc(0), zinc (II), nickel(0), nickel(II), salts thereof, complexes thereof, and any mixtures thereof.

While not limiting copper catalysts are preferred. Specifically, copper salts such as cuprous chloride, cupric chloride, copper bromide, copper iodide, copper fluoride, copper carbonate, copper sulfate, copper acetate, copper oxalate, copper thiocyanate and the like; copper containing inorganic compounds such as cuprous hydroxide, cupric hydroxide, copper cyanide, copper sulfide, copper oxide, and the like; organic copper compounds, such as copper methoxide, copper ethoxide, copper allyloxide, copper acetate, copper stearate, copper tetramethylheptanedionate, copper acetylacetonate, copper naphthenate, copper phenylate, pentafluorphenylcopper dimer, copper bis(diorganophosphate) such as copper bis(diethylphosphate) and the like; and metallic copper can be used.

No particular preparation method or purification method is required for any of the catalysts with the exception of ensuring low-moisture contents.

The catalyst can be supplied to the reaction system in the form of a mixed powder with metallic silicon or as supported with or on metallic silicon or in a fixed or non-fixed bed. If desired the catalyst and silicon metal can be subjected to an activation treatment either in the presence or absence of a microwave or RF field.

The amount of catalyst used in the invention is minimally 0.001 moles. The catalyst can be added continuously or in multiple additions over a period of time, such as, preferably, over the course of the reaction. For example, the catalyst may be added over a period of time to ensure the presence of catalyst at a sufficient level throughout the process cycle.

The solvent can be the alcohol or a suitably inert solvent. There is no specific limitation for the solvent, so far as it is inert to the silicon metal, catalyst and alcohol. However, stable solvents having a relatively high boiling temperature are preferred. Solvents transparent to microwave radiation are also preferred.

Examples of solvents include but are not limited to paraffinic hydrocarbons, such as octane, decane, dodecane, tetradecane, hexadecane, octadecane, eicosane, alkylbenzene hydrocarbons, such as diethylbenzene, cymene, butylbenzene, butyltoluene, octylbenzene, dodecylbenzene, and the like, and hydrogenated products thereof, diphenyl, diphenyl ether, monoethyldiphenyl, diethyldiphenyl, triethyldiphenyl, and hydrogenated products thereof, alkylnaphthalene hydrocarbons and hydrogenated products thereof, and triphenyl hydrocarbons and hydrogenated products thereof.

High boiling heat transfer agents include polyaromatic hydrocarbons, such as, THERMINOL and MARLOTHERM, of which MARLOTHERM is preferred. These can be used singly or in combination of two or more thereof.

The reaction can be conducted under an atmospheric, pressurized or depressurized condition. Reaction under atmospheric conditions is preferred due to the economic advantage of the simple apparatus.

The reaction is conducted at a temperature, pressure, and length of time sufficient to form the alkoxysilane. Thus, the preferred temperature is from about 100° C. to about 300° C.; the preferred pressure is atmospheric pressure, and the reaction time is from about 1 minute to about 10 hours.

The microwave reaction was carried out in a Milestone Ethos microwave unit. The Ethos can be configured to run in closed vessel or open vessel format. Both modes can be used to generate the alkoxysilanes. The Ethos unit was modified to include a pressure monitor, addition port for alcohol introduction, an entry port for a mechanical stirrer and an exit port for product collection.

The microwave power level is usually in the range of 200 to 1000 watts in a field from about 3 Hz to 300 GHz. Microwave units manufactured by other suppliers that are capable of running open and closed vessels are also appropriate for the reaction with modifications.

The reaction can be run in a batch, semicontinuous or continuous manner. In the batch reaction, the appropriate alcohol is introduced into the reaction mixture which is a slurry of metallic silicon and the copper catalyst and the reaction products are collected and purified.

In the continuous manner, the reaction slurry is continuously passed through a microwave or RF field. The alcohol and solvent are continuously recycled into the reaction mixture with product being separated and purified.

The amount of material that can be produced is limited only by the size or number of microwave generating units and the process design. In the continuous process, one preferred approach would be the use of a multiple number of microwave generators designed in parallel.

The silicon metal and catalyst can be introduced as a slurry or in a metal/catalyst bed system. The bed system can be designed to allow for replenishment of the catalyst and silicon metal as necessary. The alcohol can be introduced in conjunction with the slurry or separately. A recycle loop can be designed to ensure appropriate residence time to meet productivity requirements.

Alternatively, a reactor train can be employed wherein the slurry or reaction mixture without a fixed bed is pumped through a series of reactors to maximize residence time and productivity. After the appropriate residence time the reaction mixture is passed through an evaporation unit where ethanol is flashed off and returned to the feed unit. The reacted mixture is then transported to a vessel where the products are separated and purified by distillation.

In both the batch and continuous process the reactor can either be a traditional glass kettle or a glass tube within a microwave or RF waveguide. Other materials that are transparent to microwave or RF can be used. Additionally, the glass reactor can be enclosed within a metal jacket providing the jacket or this outer reactor does not interfere with transmission of the microwaves. In either case, the microwave or RF field generator is part of the reactor.

Depending upon whether or not the reaction mixture is slurried or the silicon/catalyst are part of a bed type system a filter may need to be installed to collect solid material prior to the mixture entering the evaporator. The above referred to evaporator will also require a chiller to condense the ethanol flashed off which can either be part of the evaporator or a separate unit.

In one preferred embodiment of the present invention, the alkoxysilane product is distilled to separate a major product from other minor products or to form a higher purity alkoxysilane.

The unreacted silicon can be recycled and design provisions can be made to add catalyst throughout the reaction if desired.

In another preferred embodiment of the present invention, any unreacted silicon metal or hydroxy compound, if present, is recycled.

In the practice of the process of the present invention, contacting is preferably carried out to produce at least a 40% conversion, more preferably at least a 70% conversion and, most preferably at least a 95% conversion.

In still another preferred embodiment of the present invention, the alkoxysilane product is the only product formed or, alternatively, is a mixture of trialkoxysilane and tetraalkoxysilane wherein the ratio of trialkoxysilane to tetraalkoxysilane is at least 2:1, more preferably at least 6:1, and most preferably the ratio of trialkoxysilane to tetraalkoxysilane is at least 9:1.

In a particularly preferred embodiment of the present invention, contacting is carried out to produce at least a 70% conversion and a ratio of trialkoxysilane to tetraalkoxysilane of at least 9:1.

The actual number of reactors required would be dependent upon the production rate. A process that has several smaller units versus one larger unit would most be preferred. A design which represents a pilot plant approach rather than a production facility approach as it utilizes several small vessels to achieve the volume equal to one large unit is preferred.

The alkoxysilanes according to the present invention have utility as coupling agents, in adhesives, sealants, construction materials, coatings, plastics, fabrics, medical devices, and cosmetics.

EXAMPLE 1

A three necked 1 liter round bottom flask inside a Milestone Multi-Syn Ethos Microwave chamber was fitted with a condenser and receiver, a mechanical stirrer, and nitrogen and ethanol inlet ports. All glassware was oven dried at 80 C and dried when set up using a heat gun and nitrogen flush. To the dried apparatus was added 20 grams (0.714 moles) of finely ground (200 mesh) silicon metal, 0.85 grams (1.66 mole %) of cuprous oxide, 1.17 grams (1.66 mole %) of cuprous chloride, 0.75 grams (1.66 mole %) of copper powder and 500 ml of Marlotherm SH. The mixture was vigorously stirred to form a slurry. The microwave unit power source was turned on with an initial power level of 975 watts and the mixture was exposed to the microwave until a temperature of 190° C. was achieved (22 minutes). The microwave power level was subsequently adjusted (335-1000 watts) over the course of the reaction to maintain the temperature at approximately 190° C. Once the reaction mixture reached 190° C., anhydrous ethanol was metered in at a rate of 8.1 milliliters/minute using a peristaltic pump. Immediately, liquid began to distill from the reaction flask with an average head temperature of 95° C. The reaction was continued until 1.5 liters of ethanol were added (185 minutes). Excess ethanol and the desired product, triethoxysilane co-distilled from the reaction mixture. The product composition was analyzed by Si-NMR spectroscopy. Silicon conversion was determined by filtering the reaction mixture and repeatedly washing the collected solid residue with hot water, acetone and diethyl ether. The silicon conversion was calculated to be 87%. Selectivity calculated from the silicon conversion was determined to favor triethoxysilane by 100%.

EXAMPLE 2

A three necked 1 liter round bottom flask inside a Milestone Multi-Syn Ethos Microwave chamber was fitted with a condenser and receiver, a mechanical stirrer, and nitrogen and ethanol inlet ports. All glassware was oven dried at 80° C. and dried when set up using a heat gun and nitrogen flush. To the dried apparatus was added 20 grams (0.714 moles) of finely ground (200 mesh) silicon metal, 0.85 grams (1.66 mole %) of cuprous oxide, 1.17 grams (1.66 mole %) of cuprous chloride, 0.75 grams (1.66 mole %) of copper powder and 500 ml of Marlotherm SH. The mixture was vigorously stirred to form a slurry. The microwave unit power source was turned on with an initial power level of 975 watts and the mixture was exposed to the microwave until a temperature of 190° C. was achieved (20 minutes). The microwave power level was subsequently adjusted (300-1000 watts) over the course of the reaction to maintain the temperature at approximately 190° C. Once the reaction mixture reached 190° C., anhydrous ethanol was metered in at a rate of 8.1 milliliters/minute using a peristaltic pump. Immediately, liquid began to distill from the reaction flask with an average head temperature of 95° C. The reaction was continued until 1.5 liters of ethanol were added (185 minutes). Excess ethanol and the desired product, triethoxysilane co-distilled from the reaction mixture. The product composition was analyzed by Si-NMR spectroscopy. Silicon conversion was determined by filtering the reaction mixture and repeatedly washing the collected solid residue with hot water, acetone and diethyl ether. The silicon conversion was calculated to be 95%. Selectivity calculated from the silicon conversion was determined to favor triethoxysilane by 100%.

EXAMPLE 3

A three necked 1 liter round bottom flask inside a Milestone Multi-Syn Ethos Microwave chamber was fitted with a condenser and receiver, a mechanical stirrer, and nitrogen and ethanol inlet ports. All glassware was oven dried at 80° C. and dried when set up using a heat gun and nitrogen flush. To the dried apparatus was added 20 grams (0.714 moles) of finely ground (200 mesh) silicon metal, 3.56 grams (5 mole %) of cuprous chloride and 500 ml of Marlotherm SH. The mixture was vigorously stirred to form a slurry. The microwave unit power source was turned on with an initial power level of 975 watts and the mixture was exposed to the microwave until a temperature of 190° C. was achieved (17 minutes). The microwave power level was subsequently adjusted (375-1000 watts) over the course of the reaction to maintain the temperature at approximately 190° C. Once the reaction mixture reached 190° C., anhydrous ethanol was metered in at a rate of 7.7 milliliters/minute using a peristaltic pump. Immediately, liquid began to distill from the reaction flask with an average head temperature of 95° C. The reaction was continued until 1.5 liters of ethanol were added (194 minutes). Excess ethanol and the desired product, triethoxysilane co-distilled from the reaction mixture. The product composition was analyzed by Si-NMR spectroscopy. Silicon conversion was determined by filtering the reaction mixture and repeatedly washing the collected solid residue with hot water, acetone and diethyl ether. The silicon conversion was calculated to be 70%. Selectivity calculated from the silicon conversion was determined to favor triethoxysilane by 100%.

EXAMPLE 4

A three necked 1 liter round bottom flask inside a Milestone Multi-Syn Ethos Microwave chamber was fitted with a condenser and receiver, a mechanical stirrer, and nitrogen and ethanol inlet ports. All glassware was oven dried at 80° C. and dried when set up using a heat gun and nitrogen flush. To the dried apparatus was added 20 grams (0.714 moles) of finely ground (200 mesh) silicon metal, 3.56 grams (5 mole %) of cuprous chloride and 500 ml of Marlotherm SH. The mixture was vigorously stirred to form a slurry. The microwave unit power source was turned on with an initial power level of 975 watts and the mixture was exposed to the microwave until a temperature of 190° C. was achieved (20 minutes). The microwave power level was subsequently adjusted (600-1000 watts) over the course of the reaction to maintain the temperature at approximately 180° C. Once the reaction mixture reached 190° C., anhydrous methanol was metered in at a rate of 7.9 milliliters/minute using a peristaltic pump. Immediately, liquid began to distill from the reaction flask. The reaction was continued until 1.5 liters of ethanol were added (189 minutes). Excess methanol and the desired product, trimethoxysilane co-distilled from the reaction mixture. The product composition was analyzed by Si-NMR spectroscopy. Silicon conversion was determined by filtering the reaction mixture and repeatedly washing the collected solid residue with hot water, acetone and diethyl ether. The silicon conversion was calculated to be 70%. Selectivity calculated from the silicon conversion was determined to favor trimethoxysilane by 100%.

EXAMPLE 5

A three necked round 1 liter round bottom flask inside a Milestone Ethos microwave unit was fitted with a condenser and receiver, a mechanical stirrer, a nitrogen line and ethanol entrance port and a thermocouple. The apparatus was dried by use of a heat gun with a continual nitrogen flush throughout the system. To the dried apparatus was added 20 grams (0.71 moles) of finely ground (200 mesh) silicone powder, 2.11 grams (3 mole %) of Cuprous Chloride and 500 ml of Marlotherm SH. The mixture was heated to 190° C. using a microwave power of up to 950 W, this taking approximately 19 minutes. The microwave power level was subsequently adjusted (385-1000 watts) over the course of the reaction to maintain the temperature at approximately 190° C. Once the reaction reached 190° C. anhydrous ethanol was metered in at a rate of 8.0 milliliters per minute using a peristaltic pump. Immediately liquid was observed to distill from the reaction flask with an average head temperature of 95° C. The reaction was continued until 1.5 liters of ethanol were added (187 minutes). The resulting distillate was collected and analyzed by Si-NMR spectroscopy for the presence of triethoxysilane, tetraethoxysilane and other alkoxysilanes. Selectivity calculated from silicon conversion was determined to favor TES at 90%. Silicon conversion was calculated to be 70%.

The present invention has been described with particular reference to the preferred embodiments. It should be understood that variations and modifications thereof can be devised by those skilled in the art without departing from the spirit and scope of the present invention. Accordingly, the present invention embraces all such alternatives, modifications and variations that fall within the scope of the appended claims.

What is claimed is:
1. A process for preparation of an alkoxysilane represented by the formula:

$$H_nSi(OR)_{4-n}$$

wherein n is from 0 to about 2; and wherein each R is independently selected from the group consisting of: a linear, branched or cyclic alkyl of having 1 to 12 carbon atoms, aryl, and acyl, wherein at least one of said alkyl, aryl and acyl groups is optionally substituted by at least one alkyl, alkoxy, halo, cyano or aryl;
said process comprising the step of:
contacting elemental silicon and an hydroxy compound represented by the formula:

ROH wherein R is selected from the group consisting of: a linear, branched or cyclic alkyl having 1 to 12 carbon atoms, aryl, and acyl, wherein at least one of said alkyl, aryl and acyl groups is optionally substituted by at least one alkyl, alkoxy, halo, cyano or aryl;
wherein said contacting is carried out in the presence of at least one catalyst selected from the group consisting of: copper, zinc, and nickel; and a non-ionizing radiation selected from the group consisting of: microwave, radio frequency (RF), and a combination thereof, and at a temperature, pressure, and time sufficient to form said alkoxysilane.
2. The process of claim 1, wherein n is from 0 to about 1.
3. The process of claim 1, wherein n is 1 or 2.
4. The process of claim 1, wherein each R is independently selected from the group consisting of: methyl, ethyl, propyl, and butyl.
5. The process of claim 1, wherein said hydroxy compound is selected from the group consisting of: methanol, ethanol, and a mixture thereof.
6. The process of claim 1, wherein said hydroxy compound is a mixture of at least two alcohols.
7. The process of claim 1, wherein said the alkoxysilane is triethoxysilane.
8. The process of claim 1, wherein said the alkoxysilane is trimethoxysilane.
9. The process of claim 1, wherein the contacting step is carried out in the presence of a solvent.
10. The process of claim 9, wherein said solvent is a non-reactive high-boiling solvent.
11. The process of claim 9, wherein said solvent is said hydroxy compound.
12. The process of claim 1, wherein said catalyst is selected from the group consisting of: copper(0), copper(I) salts, copper(II) salts, copper (II) hydroxide, zinc(0), zinc(II), nickel (0), nickel(II), salts thereof, complexes thereof, and any mixtures thereof.
13. The process of claim 12, wherein said catalyst is selected from the group consisting of: cuprous halide, cupric hydroxide, cuprous hydroxide, copper carbonate, copper sulfate, copper carboxylate, copper thiocyanate, copper cyanide, copper sulfide, copper oxide, copper alkoxide, copper tetramethylheptanedionate, copper acetylacetonate, copper naphthenate, copper phenylate, pentafluorphenylcopper dimer, copper bis(diorganophoshate) and a mixture thereof.
14. The process of claim 13, wherein said catalyst is selected from the group consisting of: copper fluoride, cuprous chloride, cupric chloride, copper bromide, copper iodide, copper methoxide, copper ethoxide, copper allyloxide, copper stearate, copper acetate, copper oxalate, copper bis(diethylphosphate) and a mixture thereof.
15. The process of claim 1, wherein said microwave is one selected from the group consisting of: a monomode microwave, a multimode microwave, and a combination thereof.
16. The process of claim 1, wherein said radio frequency is from about 3 Hz to about 300 GHz.
17. The process of claim 1, wherein said process is selected from the group consisting of: a batch process, continuous process, semi-continuous process, and a combination thereof.
18. The process of claim 1, further comprising distilling said alkoxysilane to form a higher purity alkoxysilane.
19. The process of claim 1, further comprising recycling any unreacted silicon metal or hydroxy compound.
20. The process of claim 1, wherein said catalyst is added over a period of time.
21. The process of claim 1, wherein contacting is carried out to produce at least a 40% conversion.
22. The process of claim 1, wherein the conversion is at least 70%.
23. The process of claim 1, wherein the conversion is at least 95%.
24. The process of claim 1, wherein the alkoxysilane product is a mixture of trialkoxysilane and tetraalkoxysilane.
25. The process of claim 1, wherein the alkoxysilane product is a single silane product.
26. The process of claim 24, wherein the ratio of trialkoxysilane to tetraalkoxysilane is at least 2:1.
27. The process of claim 24, wherein the ratio of trialkoxysilane to tetraalkoxysilane is at least 6:1.
28. The process of claim 24, wherein the ratio of trialkoxysilane to tetraalkoxysilane is at least 9:1.
29. The process of claim 27, wherein contacting is carried out to produce at least a 70% conversion.
30. A process for preparation of an alkoxysilane represented by the formula:

$$H_nSi(OR)_{4-n}$$

wherein n is from 0 to about 2; and wherein each R is independently selected from the group consisting of: a linear, branched or cyclic alkyl of having 1 to 12 carbon atoms, aryl, and acyl, wherein at least one of said alkyl, aryl and acyl groups is optionally substituted by at least one alkyl, alkoxy, halo, cyano or aryl;
said process comprising the steps of:
forming a slurry comprising elemental silicon and at least one catalyst selected from the group consisting of: copper, zinc, and nickel;
exposing said slurry to a non-ionizing radiation selected from the group consisting of: microwave, radio frequency (RF), and a combination thereof to until said slurry reaches a first temperature;

continuing to expose said slurry to said non-ionizing radiation while contacting said slurry with an hydroxy compound represented by the formula:

ROH wherein R is selected from the group consisting of: a linear, branched or cyclic alkyl having 1 to 12 carbon atoms, aryl, and acyl, wherein at least one of said alkyl, aryl and acyl groups is optionally substituted by at least one alkyl, alkoxy, halo, cyano or aryl to form said alkoxysilane.

* * * * *